US012559027B2

(12) United States Patent
Wilks et al.

(10) Patent No.: US 12,559,027 B2
(45) Date of Patent: Feb. 24, 2026

(54) TELETYPEWRITER SYSTEM

(71) Applicant: GM Global Technology Operations LLC, Detroit, MI (US)

(72) Inventors: Jasmine Wilks, Houston, TX (US); Kevin W. Owens, Sterling Heights, MI (US); Russell A. Patenaude, Macomb Township, MI (US); Gaurav Talwar, Novi, MI (US); Christopher L. Dow, Troy, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 91 days.

(21) Appl. No.: 18/435,775

(22) Filed: Feb. 7, 2024

(65) Prior Publication Data

US 2025/0249829 A1    Aug. 7, 2025

(51) Int. Cl.
| | |
|---|---|
| *B60Q 9/00* | (2006.01) |
| *A61B 5/00* | (2006.01) |
| *A61B 5/12* | (2006.01) |
| *B60R 11/02* | (2006.01) |
| *G09B 21/00* | (2006.01) |
| *G10L 17/22* | (2013.01) |
| *B60R 11/00* | (2006.01) |

(52) U.S. Cl.
CPC .............. *B60Q 9/00* (2013.01); *A61B 5/121* (2013.01); *A61B 5/6893* (2013.01); *B60R 11/02* (2013.01); *G09B 21/009* (2013.01); *G10L 17/22* (2013.01); *B60R 2011/0017* (2013.01); *B60R 2011/0282* (2013.01); *B60R 2011/0294* (2013.01)

(58) Field of Classification Search
CPC ......... B60Q 9/00; A61B 5/121; A61B 5/6893; B60R 11/02; B60R 2011/0017; B60R 2011/0282; B60R 2011/0294; G09B 21/009; G10L 17/22
See application file for complete search history.

(56) References Cited

U.S. PATENT DOCUMENTS

| | | | | |
|---|---|---|---|---|
| 7,433,974 B2 * | 10/2008 | Beckert | ............... | B60R 16/0315 |
| | | | | 710/22 |
| 8,600,011 B2 * | 12/2013 | Gouvia | .............. | G01C 21/3688 |
| | | | | 379/52 |
| 9,420,431 B2 * | 8/2016 | Swanson | ................. | H04W 4/14 |
| 9,544,412 B2 * | 1/2017 | Stottlemyer | ......... | H04B 1/3822 |
| 9,614,913 B2 * | 4/2017 | Ishfaq | ................ | H04M 1/6091 |
| 10,455,076 B1 * | 10/2019 | Kapadia | ................. | H04W 4/44 |
| 2008/0309820 A1 * | 12/2008 | Kostepen | ............ | B60R 11/0235 |
| | | | | 348/563 |

FOREIGN PATENT DOCUMENTS

| | | |
|---|---|---|
| DE | 102016223862 A1 | 5/2018 |
| DE | 102019114365 A1 | 3/2020 |
| DE | 102021117985 A1 | 1/2022 |

* cited by examiner

*Primary Examiner* — Gertrude Arthur Jeanglaude
(74) *Attorney, Agent, or Firm* — Honigman LLP; Matthew H. Szalach; Jonathan P. O'Brien

(57) ABSTRACT

A teletypewriter (TTY) system for a vehicle includes a display, a microphone coupled to the vehicle and configured to capture voice data, and an imager coupled to the vehicle and configured to detect image data. The TTY system includes an electronic control unit (ECU) that is communicatively coupled to the display, the microphone, and the imager. The ECU includes a TTY application and is configured to project the TTY application on the display in response to at least one of the voice data and the image data.

20 Claims, 11 Drawing Sheets

TELETYPEWRITER SYSTEM

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates generally to a teletypewriter (TTY) system for a vehicle.

In customizing a vehicle, a user is typically required to manually adjust vehicle settings by entering into system settings of the vehicle. For example, accessibility settings are typically found within audio settings of the vehicle, which can be accessed by navigating from a home or start menu. Some vehicles may also be equipped with connection capabilities for mobile devices. For example, a user may connect a mobile device, via a wire or wirelessly, to display features of the mobile device on a display of the vehicle. However, settings of the mobile device typically remain separate from the vehicle, regardless of the connectivity settings.

In a rideshare scenario, a vehicle driver may have a mobile device connected to a vehicle but a passenger may not. In this situation, connecting the passenger's mobile device to the vehicle would allow the passenger to share information with the driver. In order to do so, however, the passenger must navigate to the settings of the vehicle to establish a connection between the passenger's mobile device and the vehicle, which may be inconvenient during a rideshare scenario, which is often limited in duration and typically not repeated. Thus, there is need for improvement of ease of actuation of settings that may be advantageous or useful to users that may utilize accessibility settings both in the vehicle and on a mobile device.

SUMMARY

In some aspects, a teletypewriter (TTY) system for a vehicle includes a display and an infotainment head unit (IHU) communicatively coupled with the display. The IHU includes an electronic control unit (ECU) configured to project a TTY application on the display, and the ECU includes data processing hardware and memory hardware storing a driver profile. The data processing hardware includes the TTY application and is configured to execute the TTY application in response to at least one of a detected audio device and detected TTY settings from a user device.

In some examples, the TTY system may include a microphone communicatively coupled to the IHU and configured to capture voice data. The TTY application may be configured to execute a voice profile of the stored driver profile in response to the voice data. Optionally, the TTY system may include an imager that may be communicatively coupled with the IHU and may be configured to capture image data. The TTY application may be configured to prompt a notification in response to the captured image data. The TTY application may include accessibility settings and audio settings, and the notification may include at least one of the accessibility settings and the audio settings. In some configurations, the IHU may be coupled to a headrest of the vehicle. In other instances, the TTY application may include a hearing test, and the TTY application may be configured to execute the hearing test in response to the detected audio device. Optionally, the stored driver profile may include a digital key profile, and the TTY application may be configured to identify the digital key profile based on a detected digital key of the user device and may be configured to adjust at least one of audio settings and accessibility settings based on the identified digital key profile.

In other aspects, a teletypewriter (TTY) system for a vehicle includes a display and a microphone coupled to the vehicle. The microphone being configured to capture voice data. The TTY system also includes an imager coupled to the vehicle. The imager is configured to detect image data. The TTY system further includes an infotainment head unit communicatively coupled with each of the display, the microphone, and the imager. The infotainment head unit includes an electronic control unit being configured to project a TTY application on the display. The electronic control unit includes data processing hardware and memory hardware, and the data processing hardware includes the TTY application. The data processing hardware is configured to execute the TTY application in response to at least one of the voice data, the image data, and detected TTY settings from a user device.

In some examples, the memory hardware may store a voice profile. The TTY application may be configured to identify the voice profile based on the voice data and may be configured to execute accessibility settings based on the voice profile. Optionally, wherein the TTY application may be configured to prompt a notification in response to the detected image data. The TTY application may include accessibility settings and audio settings, the notification including at least one of the accessibility settings and the audio settings. In some instances, the infotainment head unit may be coupled to a headrest of the vehicle. In further configurations, the TTY application may include a hearing test, and the TTY application may be configured to execute the hearing test in response to a detected audio device. Optionally, the memory hardware may store a digital key profile, and the TTY application may be configured to identify the digital key profile based on a detected digital key of the user device and may be configured to adjust at least one of audio settings and accessibility settings based on the identified digital key profile.

In further aspects, a teletypewriter (TTY) system for a vehicle includes a display, a microphone coupled to the vehicle and configured to capture voice data, and an imager coupled to the vehicle and configured to detect image data. The TTY system includes an electronic control unit (ECU) that is communicatively coupled to the display, the microphone, and the imager. The ECU includes a TTY application and is configured to project the TTY application on the display in response to at least one of the voice data and the image data.

In some examples, the ECU includes memory hardware that may store a voice profile. The TTY application may be configured to identify the voice profile based on the voice data and may be configured to execute accessibility settings based on the voice profile. Optionally, the TTY application may be configured to prompt a notification in response to the detected image data. The TTY application may include accessibility settings and audio settings, and the notification may include at least one of the accessibility settings and the audio settings. In some instances, the TTY application may include a hearing test, and the TTY application may be configured to execute the hearing test in response to a detected audio device. Optionally, the memory hardware may store a digital key profile, and the TTY application may be configured to identify the digital key profile based on a detected digital key of a user device and may be configured to adjust at least one of audio settings and accessibility settings based on the identified digital key profile.

BRIEF DESCRIPTION OF THE DRAWINGS

The drawings described herein are for illustrative purposes only of selected configurations and are not intended to limit the scope of the present disclosure.

Corresponding reference numerals indicate corresponding parts throughout the drawings.

DETAILED DESCRIPTION

Figure 1:
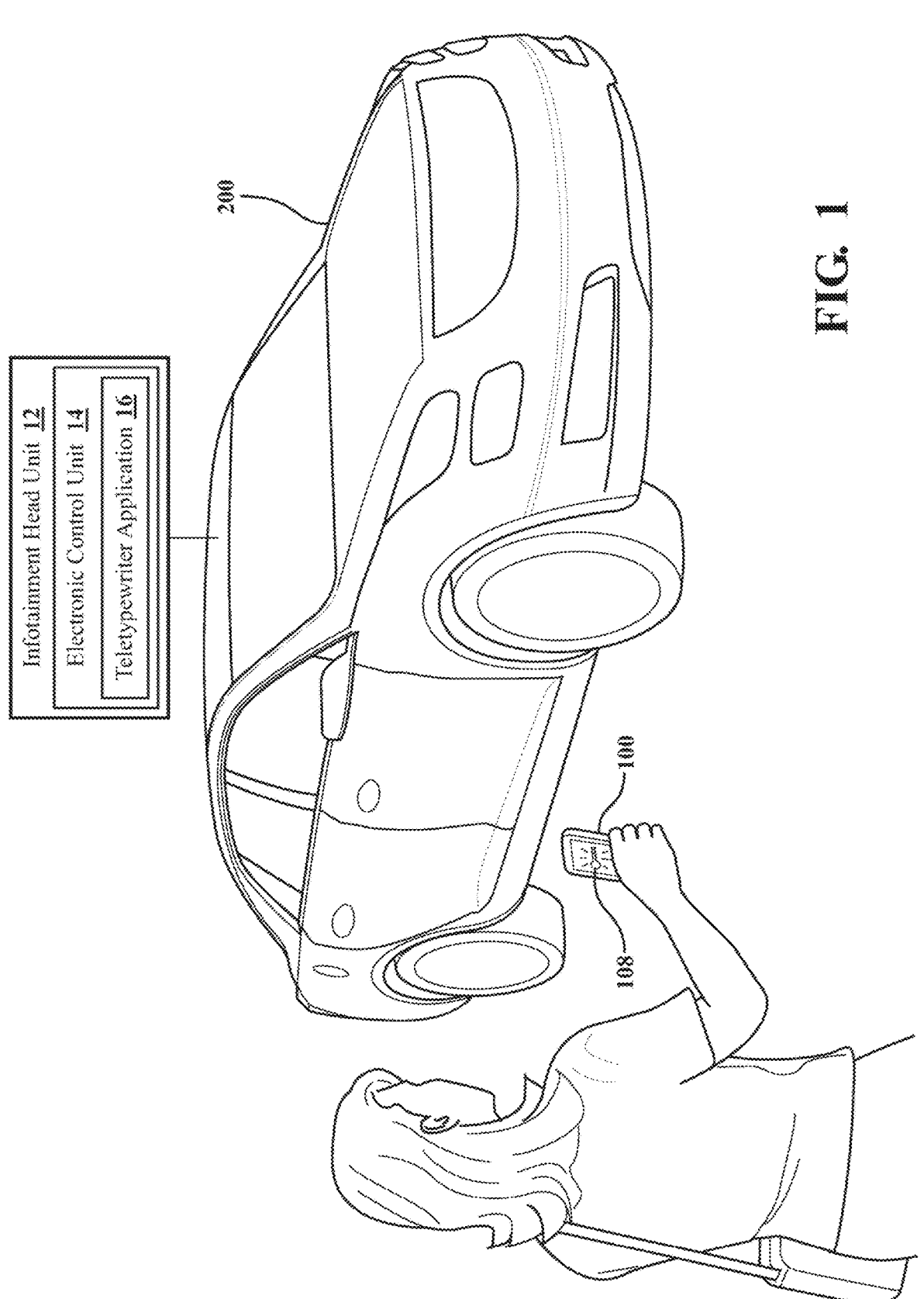
FIG. 1 is a schematic of a vehicle equipped with a teletypewriter (TTY) application according to the present disclosure, a user approaching the vehicle with a user device.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms "first," "second," "third," etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

In this application, including the definitions below, the term "module" may be replaced with the term "circuit." The term "module" may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term "code," as used above, may include software, firmware, and/or microcode, and may refer to programs, routines, functions, classes, and/or objects. The term "shared processor" encompasses a single processor that executes some or all code from multiple modules. The term "group processor" encompasses a processor that, in combination with additional processors, executes some or all code from one or more modules. The term "shared memory" encompasses a single memory that stores some or all code from multiple modules. The term "group memory" encompasses a memory that, in combination with additional memories, stores some or all code from one or more modules. The term "memory" may be a subset of the term "computer-readable medium." The term "computer-readable medium" does not encompass transitory electrical and electromagnetic signals propagating through a medium, and may therefore be considered tangible and non-transitory memory. Non-limiting examples of a non-transitory memory include a tangible computer readable medium including a nonvolatile memory, magnetic storage, and optical storage.

The apparatuses and methods described in this application may be partially or fully implemented by one or more computer programs executed by one or more processors.

The computer programs include processor-executable instructions that are stored on at least one non-transitory tangible computer readable medium. The computer programs may also include and/or rely on stored data.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Various implementations of the systems and techniques described herein can be realized in digital electronic and/or optical circuitry, integrated circuitry, specially designed ASICS (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Referring now to the figures, a teletypewriter (TTY) system 10 includes a user device 100, an audio device 102, and a vehicle 200 equipped with an infotainment head unit (IHU) 12. The IHU 12 includes an electronic control unit (ECU) 14 configured with a TTY application 16, described herein. The ECU 14 is configured to project the TTY application 16 onto a display 202 of the vehicle 200, and the TTY application 16 is executed by data processing hardware 18 of the ECU 14. The ECU 14 also includes memory hardware 20 in communication with the data processing hardware 18 and configured to store operations executed by the data processing hardware 18. The memory hardware 20 also stores a driver profile 22 that includes a digital key profile 24, a voice profile 26, and driver audio preferences 28. As described herein, the digital key profile 24 stored on the memory hardware 20 may correspond with one or more user devices 100.

The TTY application 16 includes accessibility settings 30 and audio settings 32. For example, the accessibility settings 30 may include TTY functions 30a. For example, the TTY functions 30a may provide the user with the ability to communicate using text instead of talking or listening. The accessibility and audio settings 30, 32 are configured to adjust acoustic settings of the vehicle 200. The TTY application 16 is configured to issue a notification 34 in response to the detected user device 100, described in more detail below. The notification 34 may include a hearing test 36 that may assist a user in adjusting and/or setting the accessibility settings 30. As described herein, the TTY application 16 may update the driver profile 22 in response to inputs to the IHU 12 and the hearing test 36. Thus, the results from the hearing test 36 may be stored as part of the driver audio preferences 28 within the driver profile 22. In some examples, the TTY application 16 is configured to receive TTY settings 104 from the user device 100 via a short range communication. For example, the IHU 12 and the user device 100 are each configured with short range communication to communicate with external devices. For example, the IHU 12 may communicate with the user device 100 via one or more short-range wireless communication protocols including, but not limited to, Bluetooth®, Bluetooth® Low Energy (BLE), Wi-Fi®, low frequency (LF), and ultra-wide band (UWB).

Figure 3:
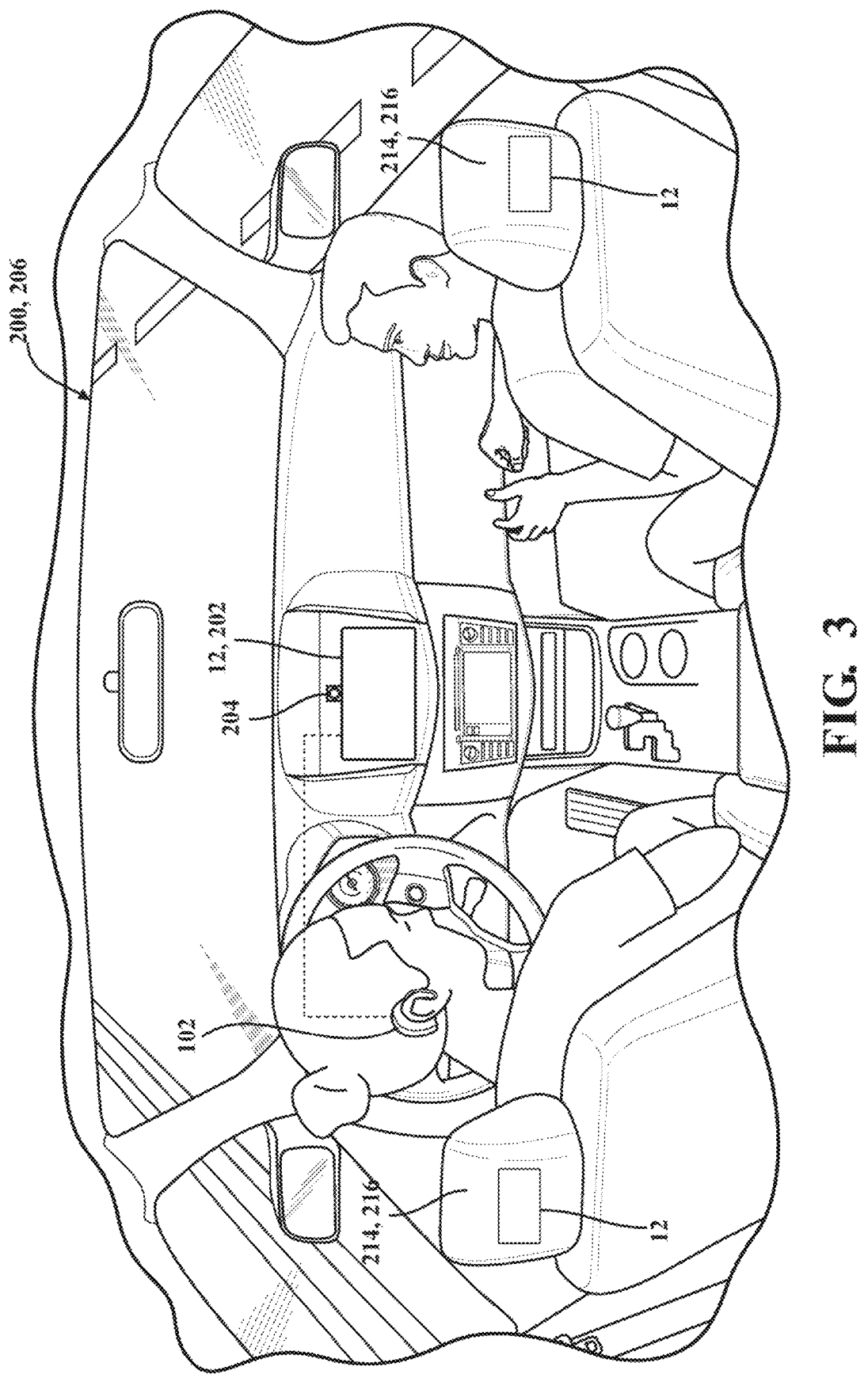
FIG. 3 is a partial perspective view of an interior cabin of a vehicle with a driver and a passenger communicating via sign language.

The audio device 102 may also be in short range communication with one or both of the IHU 12 and the user device 100. In some examples, the audio device 102 may be a hearing aid, as illustrated in FIG. 3. However, the audio device 102 may include other audio devices utilized by the user for audio purposes including, but not limited to, wireless or wired headphones. The user may utilize the audio device 102 to amplify or otherwise enhance audio signals. The TTY system 10 is configured to optionally and automatically interconnect each of the IHU 12, the user device 100, and the audio device 102. For example, the TTY application 16 may be activated upon detection of the audio device 102 by the TTY system 10, and may prompt and/or execute the hearing test 36 in response to the detected audio device 102. In some instances, the TTY application 16 may present the option of using the audio device 102 for audio output.

The user device 100 may be configured with TTY settings 104, which may be detected by the TTY application 16 upon connection with the IHU 12. The user device 100 may be connected with the IHU 12 via a media sharing application 106. The media sharing application 106 is generally configured to project media from the user device 100 onto a display 202 of the vehicle 200. The display 202 may be configured as part of the IHU 12. The TTY application 16 may receive the TTY settings 104 of the user device 100 as a result of the connection from the media sharing application 106. For example, the user may connect the user device 100 to the IHU 12 via the media sharing application 106, and the TTY settings 104 may be automatically uploaded or otherwise shared with the TTY application 16 of the IHU 12. Thus, the existing TTY settings 104 that are active on the user device 100 may be communicated with the TTY application 16. The TTY application 16 may utilize the media sharing application 106 to facilitate transfer of the TTY settings 104.

The TTY application 16 may issue the notification 34 including an option to automatically adjust the accessibility settings 30 to match the TTY settings 104 received from the user device 100. If the user authorizes the option to incorporate the TTY settings 104, then the TTY application 16 automatically updates the accessibility settings 30 and/or the audio settings 32 to reflect the TTY settings 104 from the user device 100. Thus, the user is able to readily incorporate personalized TTY settings 104 without manually navigating to the accessibility settings 30 and/or audio settings 32 via the IHU 12. In other examples, the IHU 12 may detect the audio device 102, and the TTY application 16 may issue the notification 34 including a prompt to adjust the audio settings 32. For example, the TTY application 16 may adjust the audio settings 32 to project audio from the audio device 102 instead of a speaker system of the vehicle 200.

If the user confirms the option of using the audio device 102 to play audio rather than the speaker system of the vehicle 200, then the TTY application 16 will execute and adjust the audio settings 32. Further, the TTY application 16 may prompt the notification 34 to recommend saving the audio settings 32 as part of the driver profile 22. A similar notification 34 may be issued when TTY settings 104 are received from the user device 100. Updating or saving the accessibility settings 30 and the audio settings 32 to the driver profile 22 streamlines the process in the future, such that the TTY settings 104 may be automatically set for the user upon the next use.

In some examples, the user may elect not to use the audio device 102 to project audio from the vehicle 200. In this example, the TTY application 16 may prompt the user to execute the hearing test 36. The hearing test 36 includes a series of audio signals and feedback prompts. The TTY application 16 utilizes the feedback from the user via the feedback prompts to automatically adjust the audio settings 32. While the audio signals may be projected using a speaker system of the vehicle 200, the TTY application 16 may be utilized to sharpen and tune the audio signals to maximize the user experience. Optionally, the user may elect to forego the hearing test 36 or may complete a portion of the hearing test 36. In any example, the TTY application 16 is configured to automatically adjust the audio settings 32 and may save the adjusted audio settings 32 to the respective driver profile 22.

Figure 2:
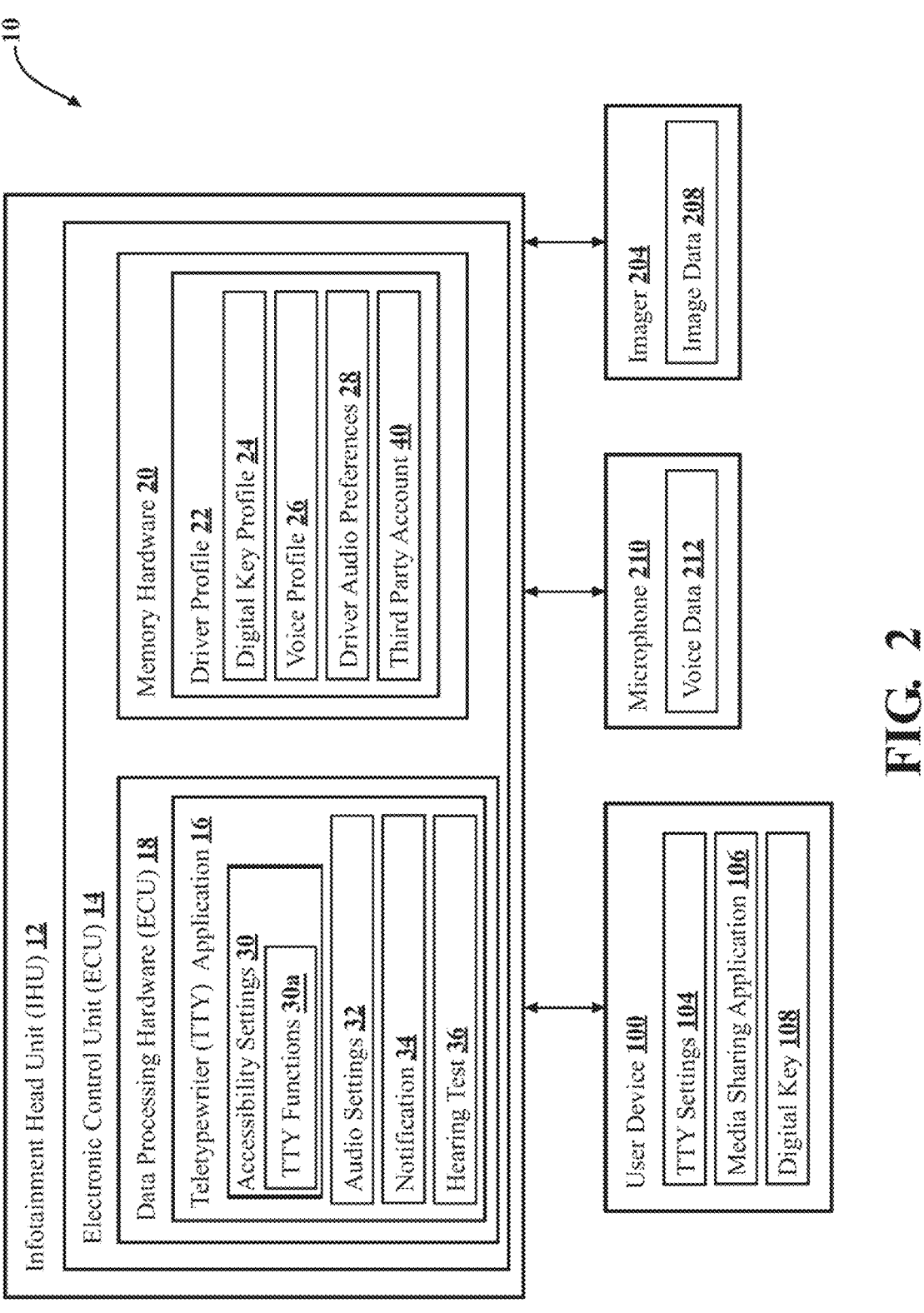
FIG. 2 is a functional block diagram of a TTY system according to the present disclosure.
Figure 4:
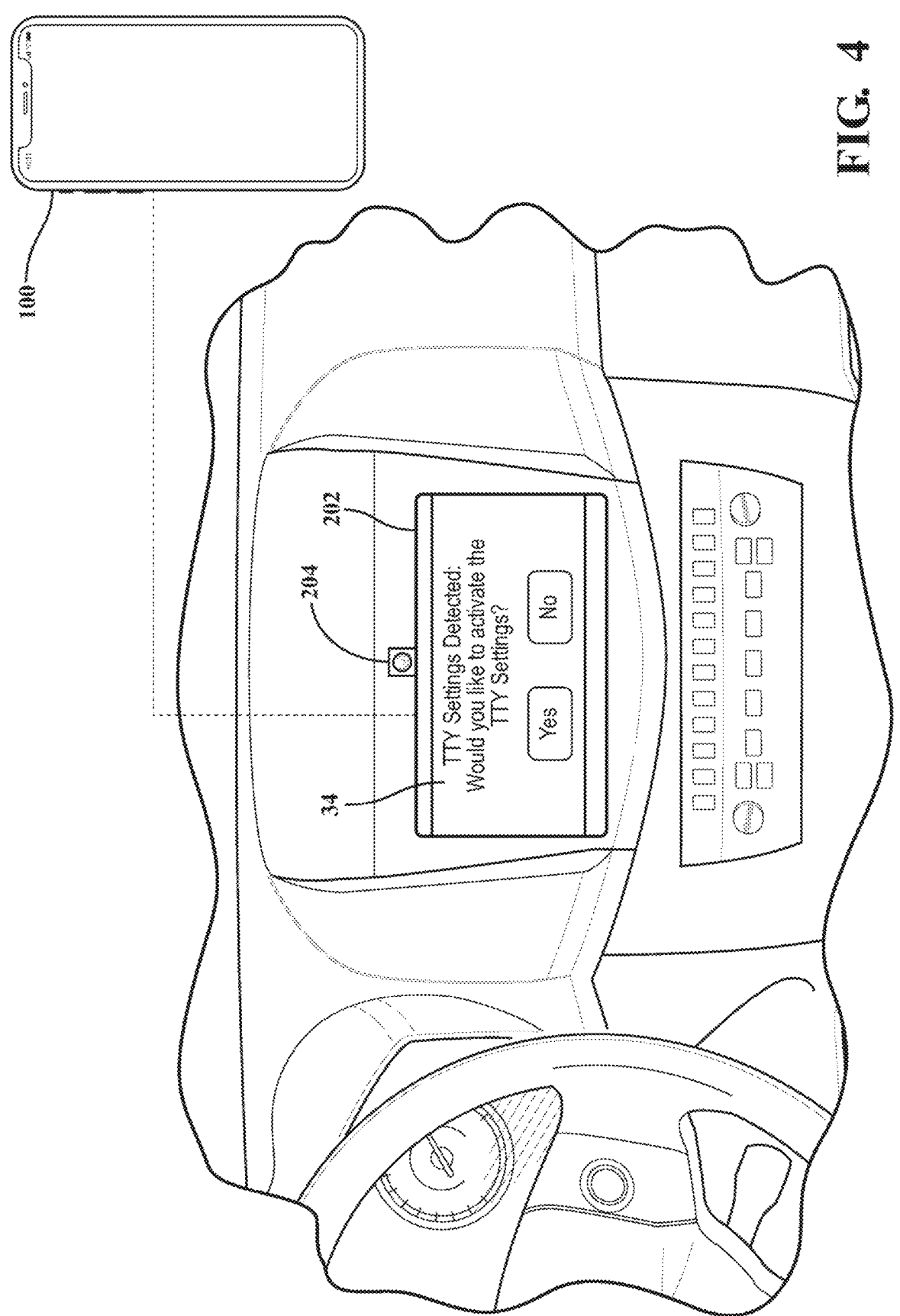
FIG. 4 is a schematic view of a TTY system according to the present disclosure in communication with a user device.
Figure 5:
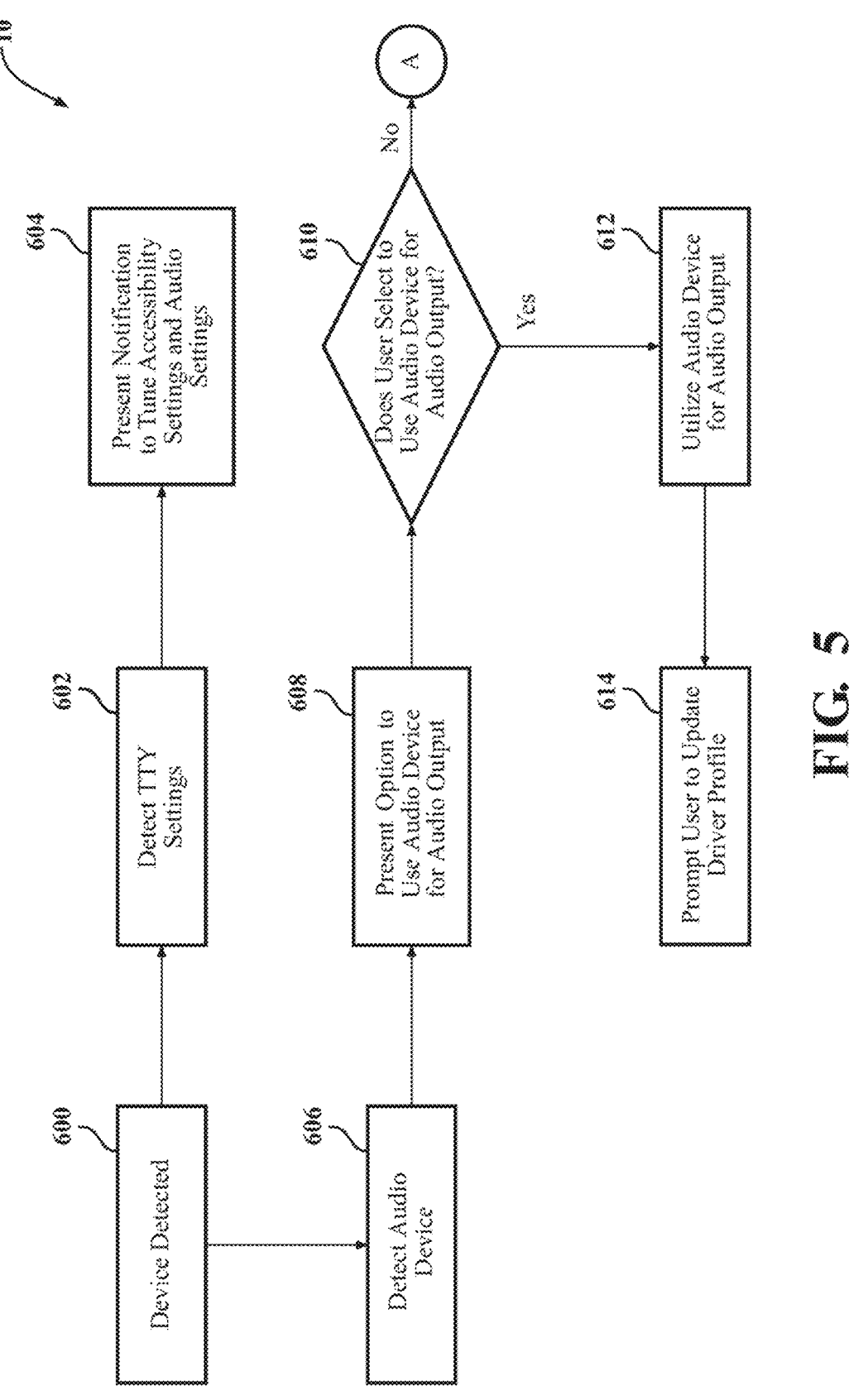
FIG. 5 is an example flow diagram for a TTY system according to the present disclosure.
Figure 6:
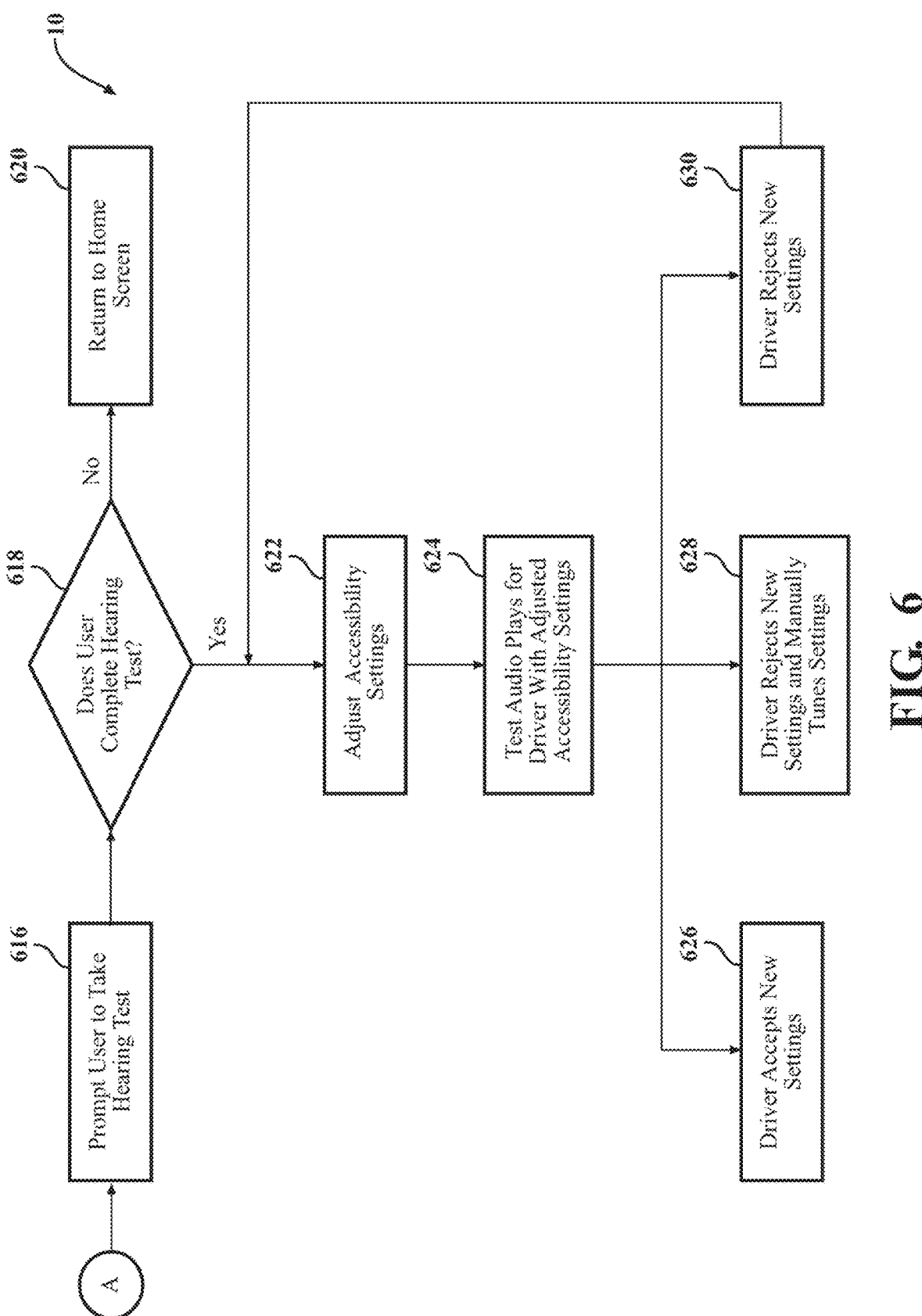
FIG. 6 is another example flow diagram for the TTY system of FIG. 5.

Referring to FIGS. 2-4, the vehicle 200 may be equipped with an imager 204 that is communicatively coupled to the IHU 12. For example, the imager 204 is depicted in FIG. 3 as being proximate to the display 202. However, the imager 204 may be positioned in any practicable location within an interior cabin 206 of the vehicle 200. The imager 204 is configured to capture and/or detect image data 208 within the vehicle 200 and communicate the image data 208 with the ECU 14 of the IHU 12. In response, the ECU 14 may activate the TTY application 16, which may be configured to prompt a notification 34 in response to the captured image data 208.

For example, FIG. 3 illustrates a passenger of the vehicle 200 communicating with sign language. The imager 204 is configured to capture the image data 208, including the use of sign language, and communicate the image data 208 with the TTY application 16. Based on the detected image data 208, the TTY application 16 may automatically adjust the accessibility settings 30 and/or the audio settings 32. In some examples, the TTY application 16, in response to the image data 208, may issue the notification 34 asking whether the user would like to activate the accessibility settings 30. As similarly described above, the user may elect to activate the accessibility settings 30 and/or may reject the notification 34.

The TTY application 16 may also be configured to automatically prompt the user with the notification 34 asking whether the user would like to activate the accessibility settings 30 in response to navigation patterns of the user. For example, the IHU 12 may detect that the user is navigating on the display 202 toward the accessibility settings 30 and/or audio settings 32 of the IHU 12. In response, the TTY application 16 may issue the notification 34 asking if the user would like to complete the hearing test 36, described above, instead of manually adjusting and tuning the settings 30, 32. If the user executes the hearing test 36, then the TTY application 16 will automatically adjust the settings 30, 32 based on the results of the hearing test 36.

As depicted in FIG. 1, the user may enter the vehicle 200 using a digital key 108. The digital key 108 may be associated with the digital key profile 24 stored as part of the driver profile 22. Thus, the TTY application 16 may recognize the driver profile 22 based on the digital key profile 24 and may automatically adjust the settings 30, 32 of the IHU 12 to correspond to any potential TTY settings 104. For example, the user may unlock the vehicle 200 using the digital key 108 on the user device 100, which alerts the TTY application 16 that a digital key profile 24 associated with a previously adjusted driver profile 22 is active. As a result, if the user has previously completed any of the processes described herein with respect to the TTY application 16, then the detection of the digital key profile 24 will trigger the TTY application 16 to execute the associated driver profile 22.

The vehicle 200 may also be equipped with a microphone 210 communicatively coupled to the IHU 12 and configured to capture voice data 212. For example, the microphone 210 may be positioned along an exterior of the vehicle 200. The voice data 212 is communicated with the ECU 14 and may be matched with the voice profile 26 of the driver profile 22. Thus, the ECU 14 may identify the user based on the voice data 212. For example, the user may state a predetermined phrase (e.g., open vehicle), and the ECU 14 will receive the voice data 212 to determine the corresponding driver profile 22. In response, the TTY application 16 is configured to execute the voice profile 26 based on the voice data 212.

Similar to detection of the digital key 108, the TTY application 16 may automatically adjust the settings 30, 32 based on the voice data 212. For example, the voice data 212 may include voice biometrics 26a stored as part of the voice profile 26. The TTY application 16 may compare the voice data 212 to the voice biometrics 26a to determine whether the user detected has previously executed the processes to customize the settings 30, 32. If the driver profile 22 is identified, then the TTY application 16 automatically adjusts the settings 30, 32 to match those previously established. Thus, the voice biometrics 26a may facilitate the tasks of the digital key 108 and may provide an alternate modality to confirm the driver profile 22.

In some examples, the user device 100 may communicate the TTY settings 104 to the ECU 14 via a third party account 40 stored as part of the driver profile 22. The third party account 40 may correspond to a third party server 300 in communication with the user device 100. For example, the user may have the third party account 40 set up and stored on the user device 100 for purposes of executing various functions on the user device 100. Upon connection of the user device 100 with the IHU 12 and/or detection of the user device 100 by the ECU 14, the third party account 40 may be identified by the ECU 14 and stored as part of the respective driver profile 22. Once the third party account 40 is stored in the driver profile 22, data associated with the third party account 40, including any TTY settings 104, may be transferred and incorporated as part of the driver profile 22.

The third party account 40 may be configured with routines 42 that may include the TTY settings 104. Upon detection of the user device 100 and identification of the third party account 40, the TTY application 16 may execute the routines 42 associated with the TTY settings 104. For example, the TTY application 16 may adjust the accessibility settings 30 in response to one of the routines 42 stored in the third party account 40. Although depicted in FIG. 2 as being stored in the memory hardware 20, the third party account 40 may first be transmitted from the user device 100.

In some examples, the routines 42 may be associated with a time-of-day that may affect the noise exterior to the vehicle 200. For example, during busier times-of-day the exterior noise may affect audio signals within the interior cabin 206 of the vehicle 200. Thus, the TTY application 16 may, based on the routine 42 and time-of-day, adjust the audio settings 32 to balance the audio signals within the interior cabin 206 relative to the exterior noise. In some instances, the TTY application 16 may first issue a notification 34 in response to detecting a routine 42 to prompt the user to elect or ignore alteration of either of the accessibility settings 30 and/or the audio settings 32.

As described herein, the TTY application 16 is configured to automatically adjust the IHU 12 to include the TTY settings 104 received from a user device 100 and/or activate driver audio preferences 28 based on a stored driver profile 22. In some examples, the vehicle 200 may be a rideshare vehicle 200 in which the user of the user device 100 is a passenger in a new vehicle 200. In this example, the IHU 12 or the rear seat entertainment (RSE) monitor may be positioned on or connected to a rear surface 214 of headrests 216 of the vehicle 200, and the user may connect the user device 100 to at least one of the displays 202 on the headrests 216 or the vehicle's IHU 12.

If a user connects to the display 202 on the headrest 216, the TTY application 16 may receive any potential TTY settings 104 from the user device 100 in the manners described herein. For example, the TTY application 16 may leverage the media sharing application 106 to gather the TTY settings 104 of the user device 100. The rideshare vehicle 200 may also be equipped with the imager 204, which may detect the use of sign language between passengers, as mentioned above. The detection of sign language may automatically prompt the TTY application 16 to issue a notification 34 on the display 202 of the passenger asking whether the passenger would like to adjust the accessibility settings 30 and/or the audio settings 32 of the IHU 12. Thus, the overall user experience for persons with hearing disabilities may be improved during a rideshare situation. Further, the driver of the rideshare vehicle 200 may have an improved ability to communicate with and an improved understanding of the passengers.

Referring now to FIGS. 1-11, a series of example flow diagrams for the TTY system 10 are described and incorporate the processes and options described herein. With specific reference to FIGS. 5 and 6, the TTY system 10 detects, at 600, a device. In some examples, the TTY system 10 detects a user device 100 and subsequently detects, at 602, TTY settings 104. The TTY system 10, via the TTY application 16, then presents, at 604, a notification 34 to tune or otherwise adjust the accessibility settings 30 and the audio settings 32. In other examples, the TTY system 10 detects, at 606, an audio device 102. In response, the TTY system 10, via the TTY application 16, presents, at 608, the option, via the notification 34, to use the audio device 102 for audio output. The TTY system 10 then determines, at 610, whether the user selected to use the audio device 102 for audio output. If yes, then the TTY system 10 utilizes, at 612, the audio device 102 for the audio output and prompts, at 614, the user to update the driver profile 22.

If the user does not select to use the audio device 102, then the TTY system 10 prompts, at 616, the user to take the hearing test 36. The TTY system 10 determines, at 618, whether the user completed the hearing test 36. If the user does not complete the hearing test 36, then the IHU 12, at 620, returns to a home screen. If the user does complete the hearing test 36, then the TTY system 10 adjusts, at 622, the interior cabin 206 acoustic settings. The TTY system 10, via the TTY application 16, then tests, at 624, audio plays for the user with the adjusted acoustic settings. The user may, at 626, accept the new settings 30, 32. In other instances, the user may, at 628, reject the settings 30, 32 and manually adjust or tune the settings 30, 32. Otherwise, the user may, at 630, simply reject the settings 30, 32, and the IHU 12 returns to the home screen.

Figure 7:
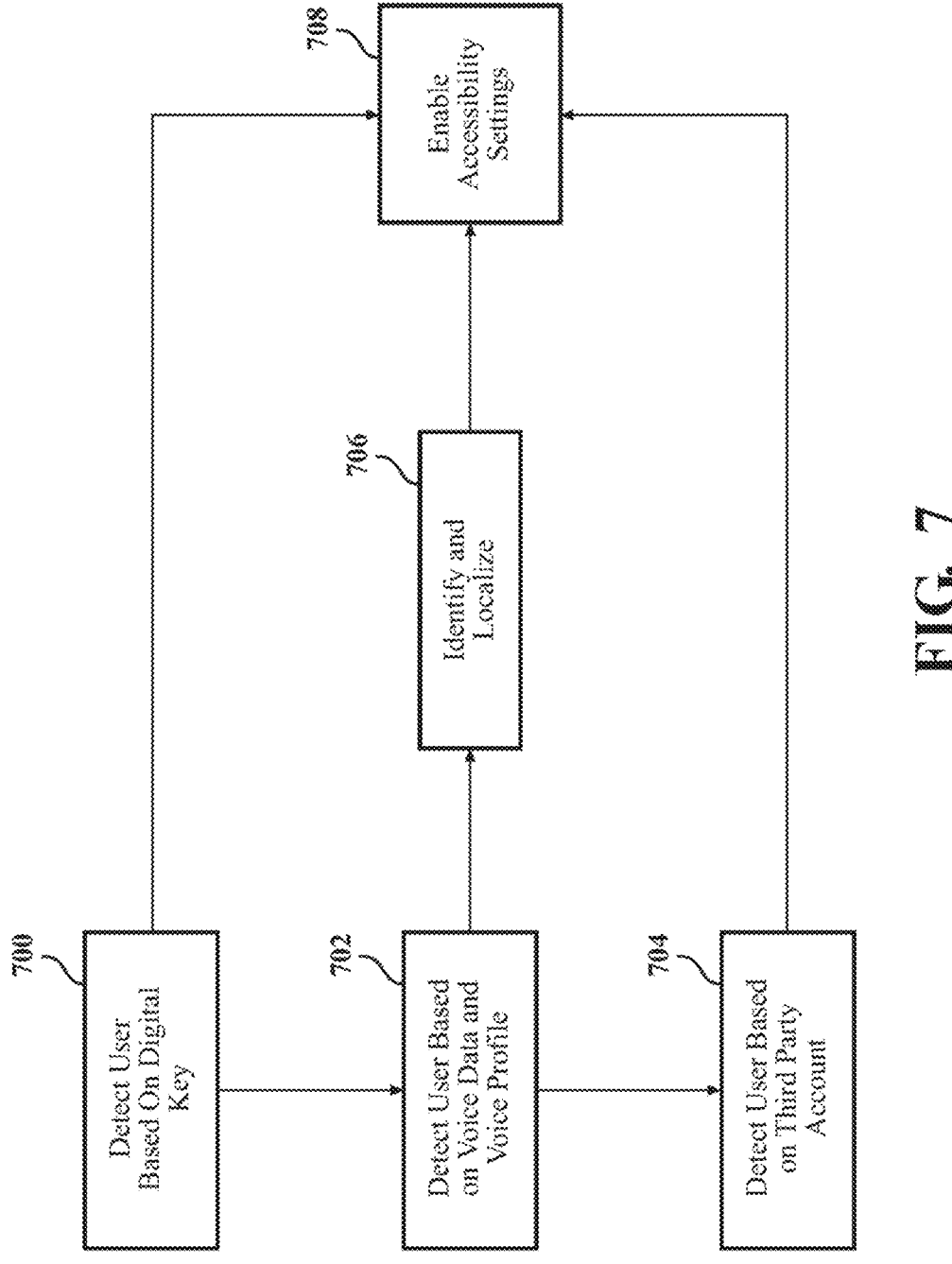
FIG. 7 is yet another example flow diagram for a TTY system according to the present disclosure.

With specific reference now to FIG. 7, another example flow diagram for the TTY system 10 is outlined. At 700, the TTY system detects a user based on a digital key 108. The TTY system 10 may also detect, at 702, the user based on the voice data 212 and the voice profile 26. Further, the TTY system 10 may detect, at 704, the user based on a third party account 40. If the TTY system 10 detects the user based on the voice data 212, then the TTY system 10 may, at 706, identify and localize the voice data 212. Once the user has been detected by the TTY system 10, the TTY system 10 may enable, at 708, the accessibility settings 30.

Figure 8:
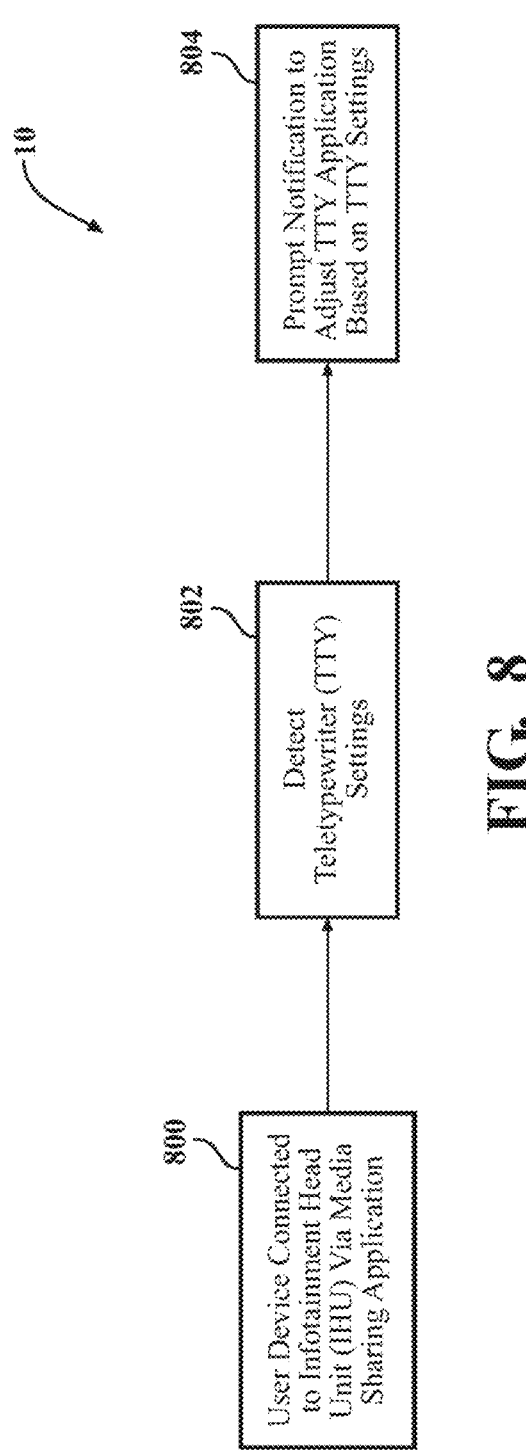
FIG. 8 is another example flow diagram for a TTY system according to the present disclosure.

Referring now to FIG. 8, another example flow diagram for the TTY system 10 is outlined. At 800, the TTY system 10 determines that a user device 100 is connected to the IHU 12 via a media sharing application 106. Through the media sharing application 106, the TTY system 10 may detect, at 802, TTY settings 104. The TTY system 10, via the TTY application 16, may prompt, at 804, a notification 34 recommending adjusting the TTY application 16 based on the TTY settings 104.

Figure 9:
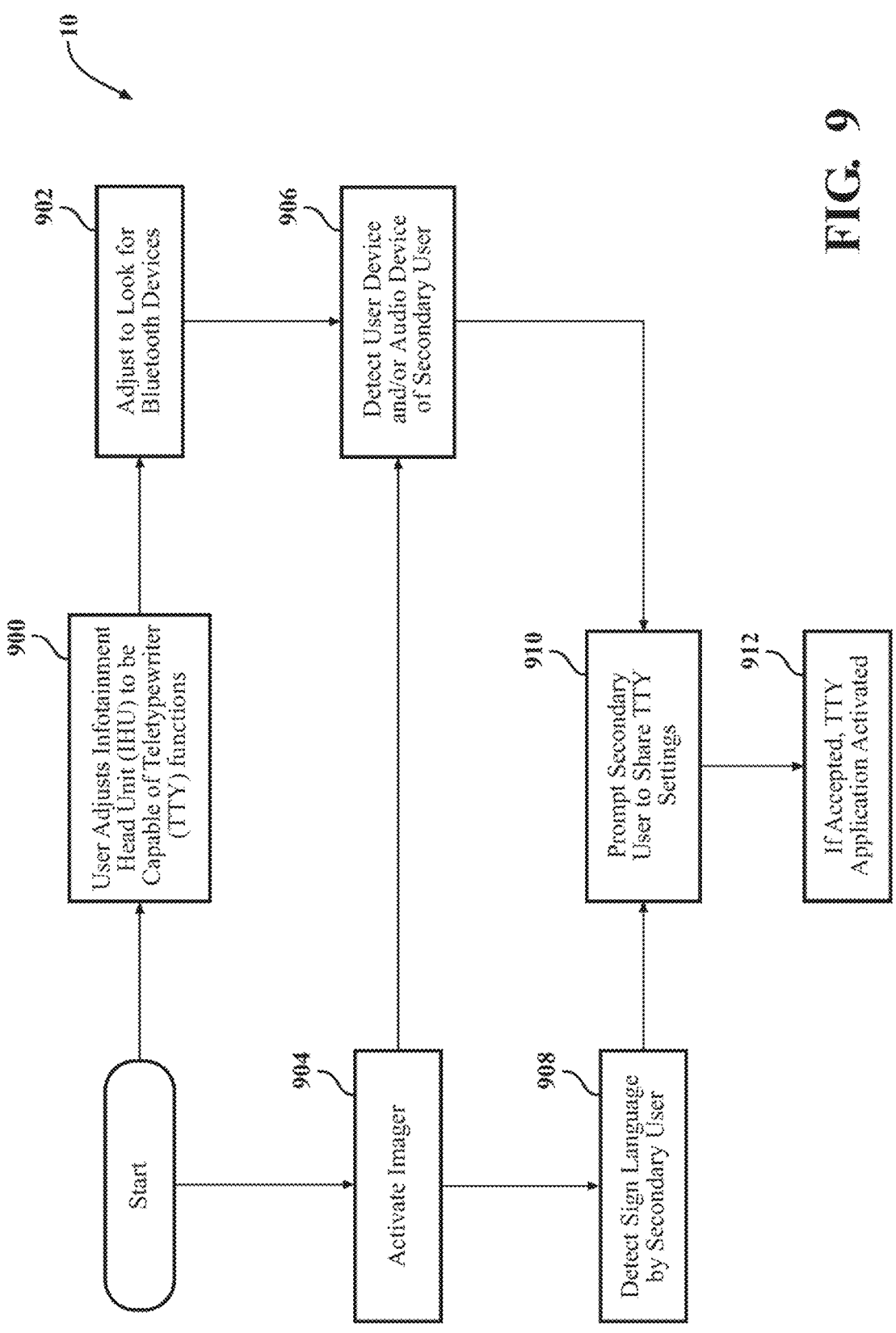
FIG. 9 is yet another example flow diagram for a TTY system according to the present disclosure.

With reference to FIG. 9, the user may adjust, at 900, the IHU 12 to be capable of TTY functions 30*a*. The TTY application 16 may be adjusted, at 902, to look for short range wireless connections. In some examples, the imager 204 is activated, at 904. The TTY system 10 may, at 906, detect the user device 100 and/or the audio device 102 of a secondary user or passenger. In some instances, the TTY system 10 may detect, at 908, sign language being used by the secondary user. In response to the detected user device 100, audio device 102, and/or the use of sign language, the TTY system 10 may prompt the secondary user to share TTY settings 104 with the IHU 12. If accepted, the TTY application 16 is activated to adjust the settings 30, 32.

Figure 10:
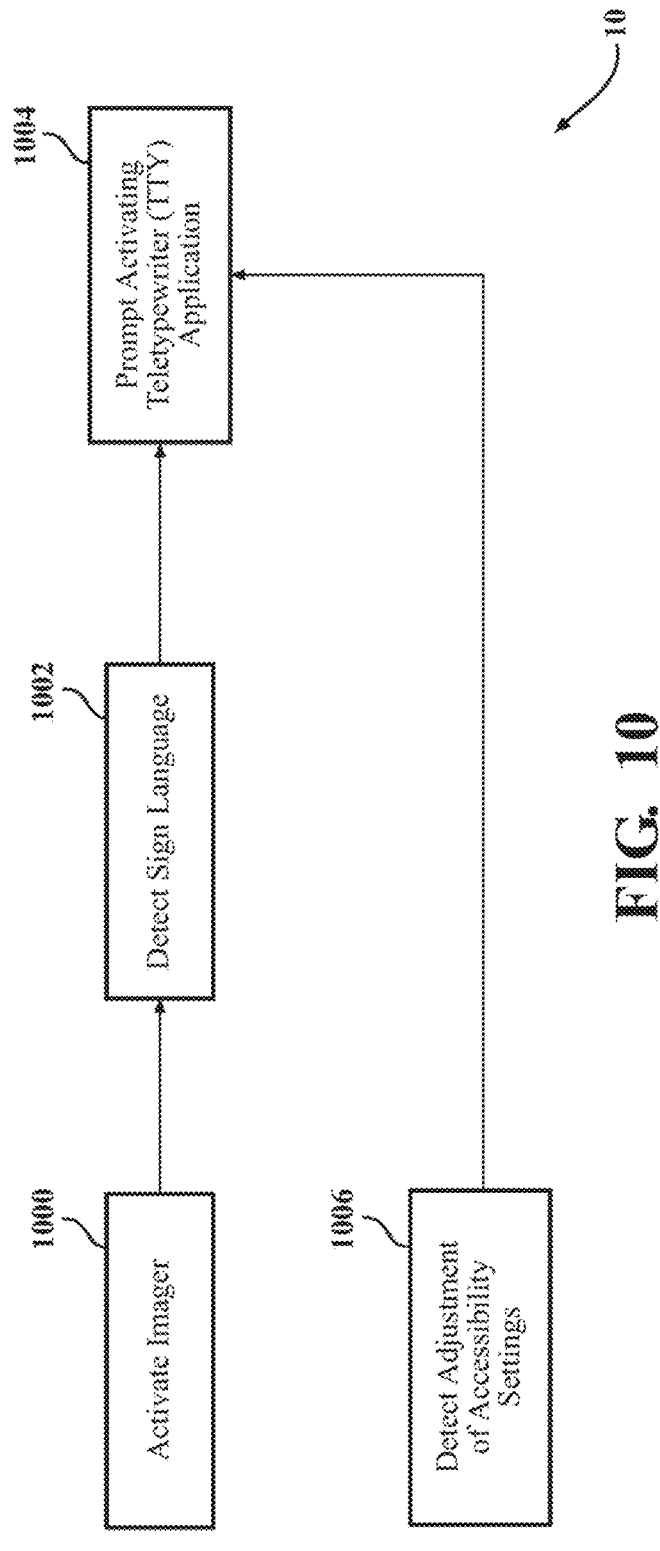
FIG. 10 is another example flow diagram for a TTY system according to the present disclosure.

Referring now to FIG. 10, the imager 204, at 1000, is activated and, at 1002, detects sign language. In response, the TTY system 10 may prompt a notification 34 to activate the TTY application 16 for adjusting the settings 30, 32. In some examples, the TTY system 10 may detect, at 1006, the adjustment of the accessibility settings 30 and will subsequently prompt the notification 34, at 1004.

Figure 11:
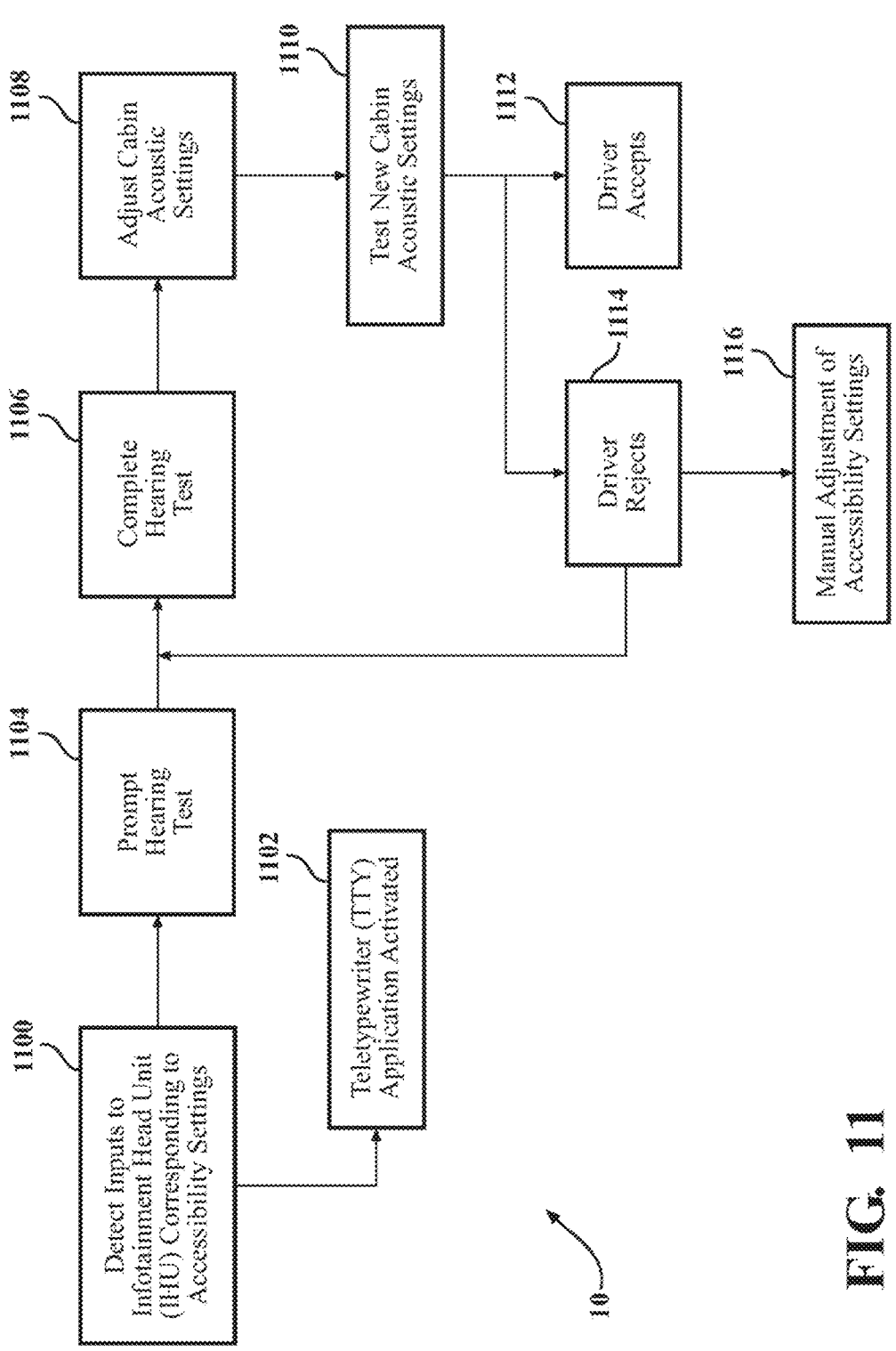
FIG. 11 is a further example flow diagram for a TTY system according to the present disclosure.

FIG. 11 illustrates another example flow diagram for the TTY system 10, where the TTY system 10 detects, at 1100, inputs to the IHU 12 corresponding to the accessibility settings 30. In response, the TTY system 10 may activate, at 1102, the TTY application 16. The TTY system 10 may also prompt, at 1104, the hearing test 36. The user may complete, at 1106, the hearing test 36, and the TTY system 10 may adjust, at 1008, the settings 30, 32. The TTY system 10 then tests, at 1110, the new settings 30, 32. The user may accept, at 1112, the settings 30, 32, or may reject, at 1114, the settings 30, 32. If the user rejects the settings 30, 32, then the user may manually adjust, at 1116, the settings 30, 32, or may return to execute the hearing test 36 again.

A number of implementations have been described. Nevertheless, it will be understood that various modifications may be made without departing from the spirit and scope of the disclosure. Accordingly, other implementations are within the scope of the following claims.

The foregoing description has been provided for purposes of illustration and description. It is not intended to be exhaustive or to limit the disclosure. Individual elements or features of a particular configuration are generally not limited to that particular configuration, but, where applicable, are interchangeable and can be used in a selected configuration, even if not specifically shown or described. The same may also be varied in many ways. Such variations are not to be regarded as a departure from the disclosure, and all such modifications are intended to be included within the scope of the disclosure.

What is claimed is:

1. A teletypewriter (TTY) system for a vehicle, the TTY system comprising:
   a display; and
   an infotainment head unit (IHU) communicatively coupled with the display and including an electronic control unit (ECU) configured to project a TTY application on the display, the ECU including data processing hardware and memory hardware storing a driver profile, the data processing hardware including the TTY application and being configured to execute the TTY application in response to at least one of a detected audio device and detected TTY settings from a user device, and wherein the TTY application includes a hearing test, the TTY application being configured to execute the hearing test in response to the detected audio device and being further configured to update the driver profile in response to the hearing test.

2. The TTY system of claim 1, further including a microphone communicatively coupled to the IHU and configured to capture voice data, the TTY application being configured to execute a voice profile of the stored driver profile in response to the voice data.

3. The TTY system of claim 1, further including an imager communicatively coupled with the IHU and configured to capture image data, the TTY application being configured to prompt a notification in response to the captured image data.

4. The TTY system of claim 3, wherein the TTY application includes accessibility settings and audio settings, the notification including at least one of the accessibility settings and the audio settings.

5. The TTY system of claim 1, wherein the IHU is coupled to a headrest of the vehicle.

6. The TTY system of claim 1, wherein the stored driver profile includes a digital key profile, the TTY application being configured to identify the digital key profile based on a detected digital key of the user device and being configured to adjust at least one of audio settings and accessibility settings based on the identified digital key profile.

7. The TTY system of claim 2, wherein the TTY application is configured to identify the voice profile based on the voice data and is further configured to execute accessibility settings based on the voice profile.

8. A teletypewriter (TTY) system for a vehicle, the TTY system comprising:
   a display;
   a microphone coupled to the vehicle, the microphone being configured to capture voice data;
   an imager coupled to the vehicle, the imager being configured to detect image data; and
   an infotainment head unit communicatively coupled with each of the display, the microphone, and the imager, the infotainment head unit including an electronic control unit being configured to project a TTY application on the display, the electronic control unit including data processing hardware and memory hardware, the data processing hardware including the TTY application and being configured to execute the TTY application in response to at least one of the voice data, the image data, and detected TTY settings from a user device, and wherein the TTY application includes a hearing test, the TTY application being configured to execute the hearing test in response to a detected audio device and being further configured to update a driver profile in response to the hearing test.

9. The TTY system of claim 8, wherein the memory hardware stores a voice profile, the TTY application being configured to identify the voice profile based on the voice data and being configured to execute accessibility settings based on the voice profile.

10. The TTY system of claim 8, wherein the TTY application is configured to prompt a notification in response to the detected image data.

11. The TTY system of claim 10, wherein the TTY application includes accessibility settings and audio settings, the notification including at least one of the accessibility settings and the audio settings.

12. The TTY system of claim 8, wherein the infotainment head unit is coupled to a headrest of the vehicle.

13. The TTY system of claim 8, wherein the memory hardware stores a digital key profile, the TTY application being configured to identify the digital key profile based on a detected digital key of the user device.

14. The TTY system of claim 13, wherein the TTY application is configured to adjust at least one of audio settings and accessibility settings based on the identified digital key profile.

15. A teletypewriter (TTY) system for a vehicle, the TTY system comprising:

a display;

a microphone coupled to the vehicle and configured to capture voice data;

an imager coupled to the vehicle and configured to detect image data; and an electronic control unit (ECU) communicatively coupled to the display, the microphone, and the imager, the ECU including a TTY application and being configured to project the TTY application on the display in response to at least one of the voice data and the image data, and wherein the TTY application includes a hearing test, the TTY application being configured to execute the hearing test in response to a detected audio device and being further configured to update a driver profile in response to the hearing test.

16. The TTY system of claim 15, wherein the ECU includes memory hardware storing a voice profile, the TTY application being configured to identify the voice profile based on the voice data and being configured to execute accessibility settings based on the voice profile.

17. The TTY system of claim 15, wherein the TTY application is configured to prompt a notification in response to the detected image data.

18. The TTY system of claim 17, wherein the TTY application includes accessibility settings and audio settings, the notification including at least one of the accessibility settings and the audio settings.

19. The TTY system of claim 16, wherein the memory hardware stores a digital key profile, the TTY application being configured to identify the digital key profile based on a detected digital key of a user device.

20. The TTY system of claim 19, wherein the TTY application is configured to adjust at least one of audio settings and accessibility settings based on the identified digital key profile.

* * * * *